United States Patent
Van Beckhoven et al.

(10) Patent No.: US 9,763,460 B2
(45) Date of Patent: *Sep. 19, 2017

(54) PURIFIED LACTASE

(71) Applicant: DSM IP ASSETS B.V., Heerlen (NL)

(72) Inventors: Rudolf Franciscus Wilhelmus Cornelis Van Beckhoven, Breda (NL); Petrus Andreas Van Paridon, Leidschendam (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/837,275

(22) Filed: Aug. 27, 2015

(65) Prior Publication Data
US 2015/0359239 A1 Dec. 17, 2015

Related U.S. Application Data

(63) Continuation of application No. 13/067,065, filed on May 5, 2011, now Pat. No. 9,149,048, which is a continuation of application No. 10/474,113, filed as application No. PCT/EP02/03680 on Apr. 3, 2002, now Pat. No. 7,955,831.

(30) Foreign Application Priority Data

Apr. 4, 2001 (EP) .................... 01000102

(51) Int. Cl.
*A23C 9/12* (2006.01)
*C12N 9/38* (2006.01)
*C12N 9/24* (2006.01)

(52) U.S. Cl.
CPC .......... *A23C 9/1206* (2013.01); *C12N 9/2402* (2013.01); *C12N 9/2471* (2013.01); *C12Y 302/01023* (2013.01); *A23C 2210/208* (2013.01); *C12Y 302/01108* (2013.01)

(58) Field of Classification Search
None
See application file for complete search history.

(56) References Cited

U.S. PATENT DOCUMENTS

| | | |
|---|---|---|
| 3,753,725 A | 8/1973 | Williams et al. |
| 3,919,049 A | 11/1975 | Kiuchi et al. |
| 4,007,283 A | 2/1977 | Crisan et al. |
| 4,237,230 A | 12/1980 | Iida et al. |
| 4,612,169 A | 9/1986 | Iwasaki et al. |
| 5,283,189 A | 2/1994 | Takase et al. |
| 5,357,852 A | 10/1994 | Kohler et al. |
| 5,821,350 A | 10/1998 | Huang et al. |
| 5,962,326 A | 10/1999 | Shimada et al. |
| 6,146,902 A | 11/2000 | McMaster |
| 7,955,831 B2 | 6/2011 | Van Beckhoven et al. |
| 2011/0212221 A1 | 9/2011 | Beckhoven et al. |

FOREIGN PATENT DOCUMENTS

| | | |
|---|---|---|
| EP | 0 020 781 A1 | 1/1981 |
| EP | 0 026 672 A2 | 4/1981 |
| EP | 0 037 667 A2 | 10/1981 |
| EP | 0 145 092 | 6/1985 |
| EP | 0 919 132 A2 | 6/1999 |
| FR | 2 500 269 | 8/1982 |
| GB | 1 306 751 | 2/1973 |
| GB | 1 477 087 | 6/1977 |
| WO | WO 01/04276 | 1/2001 |
| WO | WO 02/081673 A1 | 10/2002 |

OTHER PUBLICATIONS

Communication pursuant to Rule 114(2) EPC dated Dec. 2, 2010 with enclosed observations by a third party issued in connection with EP Appln. No. 02759791.3.
Becerra et al, "Micro-scale purification of β-galactosidase from *Kluyveromyces lactis* reveals that dimeric and tetrameric forms are active", Biotechnology Techniques 12(3):253-256 (1998).
Biochemikalien Und Reagenzien Fur Die Life Science-Forschung, Sigma (1998).
IUBMB enzyme nomenclature EC 3.2.1.23 for β-galactosidase (1980).
IUBMB enzyme nomenclature EC 3.2.1.108 for lactase (1984).
DSM Food Specialties specification sheet for Maxilact® LX5000 (May 2008).
Rahim and Lee, "Production and Characterization of Beta Galactosidase from Psychrotrophic Bacillus Subtilis KL88", Biotechnology and Applied Biochemistry 13:246-256 (1991).
Hussein et al, "Reduction of Lactose in Milk by Purified Lactase Produced by Kluyveromyces Lactis", Journal of Food Protection 52(1):30-34 (1989).
Park et al, "Production and Characterization of Beta Galactosidase EC 3.2.1.2.3 from Aspergillus Orizae", Journal of Food Science 44(1):100-103 (1979).
"Lactase (neutral)(β-galactosidase) Activity" FCC, 4th ed. pp. 801-802 (1996).
Fischer et al, "Purification and Characterization of a Thermotolerant beta-Galactosidase from Thermomyces lanuginosus", Applied and Environmental Microbiology 61(4):1497-1501 (1995).
Widmer et al, "beta-Galactosidase from Aspergillus niger: Separation and Characterization of Three Multiple Forms", European Journal of Biochemistry 100:559-567 (1979).
Product Information Sheet for "Maxilact (R)" by DSM Food Specialties [online], (no date) [Retrieved Feb. 21, 2007], Retrieved from the Internet: <URL: http://www.dsm.com/en_US/html/dfs/dairy-products-enzymes-maxilact.htm>.
NC-IUBMB (Nomenclature Committee of the International Union of Biochemistry and Molecular Biology), "Classification and Nomenclature of Enzymes by the Reactions they Catalyze", Web version of Enzyme Nomenclature 1982 [Retrieved on Jan. 23, 2007], Retrieved from the Internet: <URL: http.www.chem.qmul.ac.uk/iubmb/enzyme/ruls/html> (15 pages total).

(Continued)

*Primary Examiner* — Allison Fox
(74) *Attorney, Agent, or Firm* — Nixon & Vanderhye P.C.

(57) ABSTRACT

The present invention relates to a lactase solution comprising a lactase solution comprising less than 10 g/kg of poly and oligosaccharides, a process for the production of such a lactase solution from an untreated lactase solution, a sterilized lactase, whereby such lactose is filter sterilized in-line with the milk production process.

22 Claims, No Drawings

(56) References Cited

OTHER PUBLICATIONS

Merriam-Webster Online Dictionary definition for "Lactase" retrieved from URL: <http://www2.merriam-webster.com/cgi-bin/mwmednlm?book+Medical&va=lactase> on Jul. 9, 2008, 1 page.
Rosado et al, J. Am. Coll. Nutr. 5(3):281-290 (1986)—abstract only.
"Lactase" Merriam-Webster Online Medical Dictionary, retrieved Jul. 9, 2008 http://www2.merriam-webster.com/cgi-bin/mwmednim?book=Medical&va=lactase.
Sep. 28, 2016 Notice of Opposition of Novozymes A/S in EP1373491 (DSM IP Assets B.V.—Purified Lactase) 28 pages.
Nov. 10, 2016 Notice of Opposition of DuPont Nutrition Biosciences ApS in EP1373491 (DSM IP Assets B.V.—Purified Lactase) 43 pages.
Sep. 30, 2016 Notice of Opposition of Chr. Hansent A/S in EP1373491 (DSM IP Assets B.V.—Purified Lactase) 30 pages.
Mar. 20, 2017 Reply to Communication of notices of opposition filed by Novozymes, DuPont and Chr. Hansen in EP1373491 (DSM IP Assets B.V.—Purified Lactase) 23 pages.
Mahoney et al, "Enzymes Exogenous to Milk in Dairy Technology, Beta-D-galactose Encyclopedia of Dairy Science", (2002), Elsevier Science Ltd., pp. 907-914.
Rathore et al, "Filter Clogging Issues in Sterile Filtration", BioPharm International, Apr. 1, 2008, vol. 21, Issue 4 (5 pages).
Dickson et al, "Purification and properties of an inducible beta-galactosidase isolated from the yeast Kluyveromyces lactis", J. Bacteriol. 1979, 137(1):51-61.
Voedingsmiddelentechnologie 6 maart (1980) jaargang 13, No. 5, p. 23 "Melk met gereduceerd lactose gehalte".
Voet et al, Biochemistry, $3^{rd}$ Edition, 2004, p. 99 (Wiley International).
Albert et al, Molecular Biology of the Cell, Fourth Edition, 2002, pp. 733-735 (Garland Science).
Declaration of Morten Krog Larsen, Sep. 30, 2016 (18 pages), filed by DuPont Nutrition in Opposition to EP-B-1373491.
Cavaille et al, "Characterization of β-galactosidase from Kluyveromyces lactis", Biotechnol. Appl. Biochem. 22, 55-64 (1995).
Letter from Morgan, Lewis & Bockius LLP to Office of Food Additive Safety, FDA dated Apr. 3, 2014 re GRAS Notification for Acid Lactase from Aspergillus oryzae Expresed in Aspergillus niger submitted by DSM Food Specialities & GRAS Notification (148 pages).
Dahlqvist et al, "Hydrolysis of lactose in milk and whey with minute amounts of lactase", Journal of Diary Research (1977), 44, 541-548.
Mbuyi-Kalala et al, "Separation and characterization of four enzyme forms of β-galactosidase from Saccharomyces lactis", Eur. J. Biochem. 178, 437-443 (1988).
de Silva et al, "Purification of Microbial β-Galactosidase from Kluyveromyces Fragilis by Bioaffinity Partitioning", Revista de Microbiologia (1999) 30:324-331.
Becerra et al, "Dealing with different methods for Kluyveromyces lactis β-galactosidase purification", Biological Procedures Online, vol. 1, No. 1, May 14, 1998 (www.biologicalprocedures.com).
Steers, Jr. et al, "The Purification of βGalactosidase from Escherichia coli by Affinity Chromatography", The Journal of Biological Chemistry, vol. 246, No. 1, Issue of Jan. 10, pp. 196-200, 1971.
Tossavainen, O., "Heat-Induced Changes in Lactose Hydrolysed Milks", Doctoral Dissertation, Helsinki Univeristy of Technology, 2008 (74 pages).
Richmond et al, "Beta-Galactosidase: Review of Recent Research Related to Technological Application, Nutritional Concerns, and Immobilization", 1981 J. Dairy Sci 64:1759-1771.
Mahoney et al, "Purification and Physicochemical Properties of β-Galactosidase from Kluyveromyces fragilis", Journal of Food Science, vol. 43, pp. 584-591 (1978).
Mittal et al, "The Effect of Protease Contamination in Lactase on the Flavour of Lactose-Hydrolyzed Milks", The Australian Journal of Dairy Technology, pp. 46-48, May 1991.
Weiqun et al, "Purification and Characterization of Beta-galactosidase from Kluyveromyces lactis", Chinese Journal of Biotechnology 9(4):348-354, 1993.
Jieyan et al, "Lactose Hyrolysis of Milks by Kluyveromyces lactis Lactase", Food & Fermentation Industries 1991, No. 3 (7 pages).
Coenen et al, "Safety evaluation of a lactase enzyme preparation derived from Kluyveromyces latis", Food and Chemical Toxicology 28 (2000) 671-677.
de Vrese et al, "Probiotics—compensation for lactase insufficiency[1-3]", Am J Clin Nutr 2001; 73(suppl):421S-9S, 2001.
Sigma, Chemie, Biochemikalien Organische Verbindungen Und Diagnostika, Alphabetical Listing of Compounds, pp. 492-493 (1996).
Portnoy et al, "Separation of Alternaria into protein and carbohydrate fractions with phenyl Sepharose", J Allergy Clin Immunol 1991; 87:789-93.
Brochure, Tetra Aldose, "Aseptic in-line dosing", 2011 Tetra Pak Diary & Beverage Systems.
Pereira-Rodriguez et al, "Structural basis of specificity in tetrameric Kluyveromyces lactis β-galactosidase", Journal of Structural Biology 177 (2012) 392-401.

US 9,763,460 B2

PURIFIED LACTASE

This application is a continuation of U.S. patent application Ser. No. 13/067,065, filed May 5, 2011 (published as US 2011-0212221 A1, issued as U.S. Pat. No. 9,149,048 on Oct. 6, 2015), which is a continuation of U.S. application Ser. No. 10/474,113, filed Oct. 6, 2003 (issued as U.S. Pat. No. 7,955,831 on Jun. 7, 2011), which is the U.S. national phase of international application PCT/EP2002/003680 filed on Apr. 3, 2002, which designated the US and claims priority to EP Application No. 01000102.2, filed Apr. 4, 2001. The entire contents of these applications are incorporated herein by reference.

FIELD OF THE INVENTION

The present invention relates to purified lactase and the production thereof.

BACKGROUND OF THE INVENTION

Lactase or beta-galactosidase (EC: 3.2.1.23) is an enzyme, which can convert lactose (disaccharides) into the monosaccharides glucose and galactose. Lactose is present in dairy products and more particularly in milk, skimmed milk, cream and other milk products. The breakdown of lactose occurs in the intestinal wall of the human body (and in other mammals) by the natural presence of lactase.

Many humans (and other mammals) suffer from lactose-intolerance, wherein lactase is absent or partially absent in their digestive system. In case where lactose is part of the food or feed, decreased digestion of lactose may lead to intestinal trouble.

Nowadays lactase is added to milk to breakdown the lactose present. Lactase may be added to milk either before or after pasteurisation or sterilization. In general lactase will be inactivated during pasteurisation or sterilization treatment. When lactase is added before sterilization a large amount of lactase may be required in order to reduce the storage time between addition and pasteurisation/sterilization. Although lactase is an active enzyme one has to keep in mind that milk is processed and stored generally at temperatures between 0 and 8° C.

The other possibility is the addition of the enzyme after pasteurisation or sterilization of the milk and before packing. In this case lactase may be added in a lower amount, as it may be at least 10 to 24 hours before the milk is consumed. The enzyme can digest lactose, which may be present during transport and storage in the factory, shop and in the refrigerator of the consumer.

There are several ways to sterilize lactase, for example by chemical and/or heat treatment. However, because of its application in food or feed, sterile filtration is a preferred option.

In the journal Voedingsmiddelentechnologie 13 (1980), 23, a method, which is also described in British patent specification 1477087, is further illustrated. Lactase, usually used by the dairy processing industry as an aqueous solution to which one or more stabilizing agents, such as glycerol, can be added, is filtered before use. The filtered enzyme solution is pumped through a sterile filter then injected via a dosing device into a production line of previously sterilized or pasteurised milk and then mixed with the milk which is subsequently packed under aseptic conditions in uniform packs.

However, in practice, the sterile filter often blocks due to degraded protein, poly- and oligosaccharides remaining in the enzyme solution despite filtering. According to EP 145092, such degradation generally increases the longer the enzyme is stored prior use and may be promoted by the considerable period of time between the production of the enzyme and its use in the dairy processing industry. The repeated cleaning or replacement of the sterile filters is not an option since stopping the whole process requires sterilisation before starting again.

EP 145092 describes a process for the sterile filtration of lactase within 14 days of it being produced. EP 145092 describes that lactase should be sterile filtered after recovery and purification of lactase produced by fermentation, but before the formation of degradation products which are sufficient to clog the sterile filter. However the approach of sterile filtering freshly produced lactase solution does not fulfil the need of lactase solution which can be filtered in-line and which can be added to the sterilized/pasteurised milk. The lactase described in EP 145092 is derived from the yeast *Kluyveromyces* that is used widely in the dairy industry. The polysaccharides are probably parts of host cell walls, which are formed during the recovery process.

SUMMARY OF THE INVENTION

The present invention provides a lactase solution comprising less than 10 g/kg of poly and oligosaccharides.

The present invention also provides a process for the production of a lactase solution, whereby the poly and oligosaccharides present in an untreated solution are separated from the lactase solution.

The present invention also provides a process for producing lactase containing milk whereby the lactase is sterilized before the lactase is added to the milk.

The present invention also provides a sterilized lactase solution and also dairy products comprising the sterilized lactase solution.

DETAILED DESCRIPTION OF THE INVENTION

The present invention relates to purified lactase and in particular to novel processes for the production of lactase free from poly and oligosaccharides. The removal of poly and oligosaccharides allows easier filter sterilization of the lactase solution since the filter does not become blocked with poly and oligosaccharides. As a result, purified lactase can be filter sterilized "in line" with a milk production process, thereby negating the need for such a filter to be repeatedly unblocked.

The present invention provides a solution of lactase, which can be stored and which, after storage, is still free of clogging compounds such as poly and or oligo saccharides. Preferably this solution can be stored after recovery and purification from the fermentation process for at least 15 days, preferably more than 30 days and more preferably more than 120 days.

Free of poly- and oligosaccharides means that less than 10 g/kg of poly- and oligosaccharides are present in the lactase solution. Preferably less than 5 g/kg, more preferably less than 2 g/kg and most preferably less than 1 g/kg of poly- and oligosaccharides are present in the lactase solution.

The lactase solution of the present invention is very suitably of sterile filtration, since the low concentration of compounds such as poly- and oligosaccharides, allows the lactase solution to be sterile filtered with less chance of clogging the filter. The filter can be used for a long time preferably at least four times longer than in case of use of lactase solution, which is not substantially free of polysaccharides.

The lactase solution is preferably an aqueous solution of lactase. The lactase solution in general will contain from 10 to 100000 NLU/g, preferably from 100 to 10000 NLU/g.

The lactase solution may comprise one or more solvents or other additives, which bring the enzyme activity to the desired level and may further stabilize the enzyme. Suitable solvents are, for example, sorbitol and glycerol. These solvents may be added to a concentration of from 10 to 70 w/w %, or more preferably 30 to 70% w/w, of the lactase solution. Suitable additives, which stabilize the enzyme, are for example, hydrolysed lactose, glucose, mannitol and salt buffers. According to one embodiment of the present invention the lactase solution, which is generally free of clogging compounds such as polysaccharides, can be obtained by purifying an untreated lactase solution in a chromatographic process whereby all the compounds responsible for clogging a filter are separated from the lactase solution.

Even in cases where the untreated lactase solution is stored for at least 15 days or even more than 30 days before the chromatographic process, the purified lactase solution can still be easily sterile filtered without the filter becoming clogged.

Unexpectedly, the use of chromatography makes it possible to remove all (poly- and oligosaccharides, proteins, peptides etc.) compounds, which might clog the sterile filter. Surprisingly, it was found that only one chromatographic step was required to remove all polysaccharides and all other unknown non-protein compounds, which are responsible for clogging the sterile filter. One has to keep in mind that the lactase solution although being recovered and purified from the fermentation broth, will contain at least polysaccharides, which are at least partly converted into degradation products. Typical concentration of polysaccharides in untreated lactase solutions are from 10 to 100 g/kg.

Commercial lactase preparations may contain from 40 to 60% w/w of glycerol. The viscosity of the lactase preparation is therefore expected to be related to the amount of glycerol present. However we have found the viscosity of a lactase preparation can be reduced significantly by the removal of polysaccharides from the lactase preparation. This reduction of viscosity makes it possible to pass the lactase preparation through the sterile filter at a reduced pressure difference or at similar pressure difference on the filter, to allow more lactase solution to pass through the filter compared to a lactase solution not purified according to the present process. The invention provides lactase solutions comprising from 10 to 70 w/w % of glycerol, preferably 30 to 70 w/w % and more preferably 40 to 70 w/w % of glycerol having a viscosity of less than 100 mPa, preferably less than 80 mPa and even more preferably less than 60 mPa.

Separation of the clogging compounds from the lactase solution can be achieved by binding of the lactase to an appropriate chromatographic resin. Suitable resins which can be used to separate clogging compounds from a lactase solution are for instance anion and cation exchange resins. Anion exchangers, for instance Q-sepharose, can be used when a lactase solution at a pH above its isoelectric point is applied to an anion exchanger equilibrated in the same pH. Lactase, but not clogging components, is bound to the resin. The bound lactase can be eluted (desorbed), free of clogging compounds, from the resin by increasing the ionic strength and/or changing the pH of the anion exchange resin. The change in ionic strength and/or pH during desorption or elution can take place under a stepwise or continuous gradient.

The same separation can be achieved with a cation exchanger, for instance SP-sepharose, wherein the lactase preparation is applied to the resin below its isoelectric point. We have found that HAP (hydroxyapatite) chromatography does not give separation of the poly and oligosaccharides from the lactase. A possible explanation might be that poly and oligosaccharides are also bound to the HAP matrix.

Preferred resins are hydrophobic interaction media (HIC). On a HIC media, separation can be obtained based on the differences in hydrophobicity. Different HIC resins are available which contain different ligands, for instance ethyl, propyl, butyl, phenyl and octyl. By applying an aqueous lactase solution under conditions which, permit binding of lactase to the resin, it is possible to separate lactase from the clogging compounds.

A typical protocol for promoting binding or adsorption to a HIC resin is applying an aqueous lactase solution under non-denaturing pH and a relatively high ionic strength to the resin. The high ionic strength can be obtained by adding salts to the lactase solution. Appropriate salts are for instance ammonium sulphate, sodium chloride and sodium sulphate.

After the binding or adsorption step, lactase can be eluted or desorbed by decreasing the ionic strength. The change in ionic strength and/or pH during elution or desorption can take place under a stepwise or continuous gradient. Other suitable resins are for instance gelfiltration media and hydrophobic charge induction media (combination of HIC and ion exchange chromatography).

The lactase provided in the present invention produced by a yeast, preferably a *Kluyveromyces* strain more preferably *K. lactis* or *K. fragilis*. Such lactase is purified according to the invention resulting in a lactase solution which is easy to sterilize. The removal of all compounds responsible for clogging the sterile filter is very surprising because after the fermentation process, the lactase, which is being recovered and purified, may contain polysaccharides, which are at least partly converted into degradation products. Therefore it is believed that protease and other contaminating proteins also present in lactase solution are removed in the chromatography step. The sterile filter preferably used to sterilize the lactase solution is in general present in the milk in-line production process. The sterile filtering treatment is preferably carried out in-line with respect to the milk production process, whereby one or more membrane filters are used. A suitable sterile filter is for example a membrane filter having a pore size of 0.22 µm.

The lactase solution according to the invention is advantageously used in the preparation of pasteurised milk.

Example 1

The example describes a typical chromatographic purification procedure of lactase using phenyl sepharose LS as chromatographic resin.

The commercial product Maxilact® 5000 LX (obtainable from DSM, The Netherlands) containing 5000 NLU/g was diluted 5 times with demineralised water, ammonium sulphate is added to a final concentration of 1 M after which the pH was corrected to 7.5.

A 20 ml sample was applied to a 20 ml HiPrep phenyl 16/10 column having a diameter of 16 mm and length of 10 cm, at a linear flow rate of 150 cm/h. The column was equilibrated with 1 M ammonium sulphate in 100 mM Tris pH 7.5. After loading the column was washed with equilibration buffer at a flow rate of 150 cm/h until the baseline was reached. Elution of lactase was done under a step gradient at 150 cm/h (100 mM Tris pH 7.5). After elution of the lactase the lactase solution was desalted and concentrated to a final activity of approximately 10.000 NLU/g. After concentration the lactase solution was formulated with glycerol at a final concentration of 50% w/w, the final lactase activity after formulation is approximately 5.000 NLU/g.

Lactase activity was determined by the hydrolysis of the substrate o-nitrophenyl-β-galactopyranoside (ONPG) into o-nitrophenyl and galactose. The reaction was terminated by the addition of sodium carbonate. The absorbance of the o-Nitrophenyl formed, being yellow in alkaline medium, was used to measure the activity of the enzyme (expresses as NLU/g). The procedure is published in the. *FCC, fourth edition*, Jul. 1, 1996, page 801 to 802/*Lactase (neutral) (β-galactosidase) activity*

The results are shown in the Table 1

TABLE 1

| Sample | Activity NLU/g | g/kg sugars before inversion | g/kg sugars after inversion | Poly- and oligosaccharides g/kg |
|---|---|---|---|---|
| Maxilact LX 5000 | 5000 | 1 | 57.6 | 56.6 |
| Purified Lactase | 5000 | <1 | 2.21 | <2 |

Poly- and oligosaccharide content was determined by measuring the amount of free sugar and the amount of sugar present after the acid inversion of the polysaccharides.

The polysaccharide contents were determined by means of High Performance Liquid Chromatography (HPLC). The detection was performed using a RI (refraction index)-detector. The column used was a BioRad Aminex HPX 87N, length 30 cm, inner diameter 7.8 mm, thermostated at 85° C. The mobile phase was a solution of 0.71 g sodium sulphate in 1 liter water at a flow rate of 0.68 ml per minute.

Two different samples pre-treatment were performed, both with and without acid inversion. The sample pre-treatment without inversion was done by weighing 5 g sample in a volumetric flask of 50 ml, dissolving in mobile phase and injecting 5 μl onto the column.

The sample pre-treatment with inversion was done by weighing 2 g sample in a centrifuge tube, adding 3.00 ml water and 2.50 ml hydrochloric acid 2.58 mol/l, heating for 75 minutes at 100° C. and adding 2.50 ml sodium hydroxide 2.58 mol/l. 5 μl of the resulting solution was injected onto the column.

The glucose content was calculated using a standard solution with a concentration of 400 mg glucose in 50 ml mobile phase. The concentrations of trisaccharide, disaccharide and fructose were calculated using a response factor, relative to glucose.

Example 2

The example describes the sterile filtration of lactase solutions.

A syringe was filled with 1 ml Maxilact LX 5000, and a sterile filter, Millex GV 0.22 μm from Millipore with a surface of 4.91 cm$^2$, was placed on top of the syringe. After applying hand pressure it was not possible to filter the product through the filter, increasing the pressure caused the filter to break.

Another syringe was filled with 1 ml of purified lactase formulated with 50% w/w glycerol (end concentration), prepared as described in Example 1, and a sterile filter, Millex GV 0.22 μm from Millipore with a surface of 4.91 cm$^2$, was placed on top of the syringe. After applying hand pressure it was surprisingly easy to sterile filter at least 1 ml of the lactase solution through the filter.

Therefore, the use of chromatography allowed all compounds which may have clogged the sterile filter to be removed, and as a result sterile filtration was not problematic.

Example 3

The example describes viscosity measurements of formulated lactase solutions.

The viscosity of both the commercially available Maxilact LX 5000 and of the purified lactase formulated with 50% w/w glycerol (end concentration), prepared as described in Example 1 was measured. Commercially available Maxilact also contains 50% w/w glycerol.

The viscosity was measured with a Physica UDS 200 at 25° C., using a MK 21 cone probe.

Table 2 shows the viscosity of the purified lactase formulated at 5.000 NLU/g with 50% glycerol (end concentration) significantly drops as a result of the purification in which all clogging compounds are removed.

TABLE 2

Results of viscosity measurements

| Product | Viscosity mPa shear rate = 100 (s−1) |
|---|---|
| Commercial Maxilact LX 5000 | 170 |
| Purified lactase formulated with 50% glycerol | 40 |

We claim:

1. A process for producing lactase containing milk whereby a lactase solution comprising less than 10 g/kg of poly and oligosaccharides is sterilized before addition to the milk and wherein sterilization is carried out on at least one filter positioned in line with the milk production process.

2. A process according to claim 1 whereby the milk is pasteurized or sterilized milk.

3. A process according to claim 1, wherein said lactase solution after storage for at least 15 days comprises less than 10 g/kg of poly and oligosaccharides.

4. A process according to claim 2, wherein said lactase solution after storage for at least 15 days comprises less than 10 g/kg of poly and oligosaccharides.

5. A process according to claim 2, wherein said lactase solution is an aqueous solution.

6. A process according to claim 2, wherein said lactase solution is an aqueous solution.

7. A process according to claim 1, wherein said lactase solution further comprises a stabilizing solvent.

8. A process according to claim 2, wherein said lactase solution further comprises a stabilizing solvent.

9. A process according to claim 7, wherein the stabilizing solvent is sorbitol or glycerol.

10. A process according to claim 8, wherein the stabilizing solvent is sorbitol or glycerol.

11. A process according to claim 1, wherein said lactase solution further comprises at least one stabilizing additive.

12. A process according to claim 2, wherein said lactase solution further comprises at least one stabilizing additive.

13. A process according to claim 11, wherein the additive is selected from hydrolysed lactose, glucose, mannitol and salt buffers.

14. A process according to claim 12, wherein the additive is selected from hydrolysed lactose, glucose, mannitol and salt buffers.

15. A process according to claim 1, wherein the lactase solution contains from 10 to 100,000 NLU/g.

16. A process according to claim 2, wherein the lactase solution contains from 10 to 100,000 NLU/g.

17. A process according to claim 1, wherein the lactase is produced in a *Kluyveromyces* strain.

18. A process according to claim 2, wherein the lactase is produced in a *Kluyveromyces* strain.

19. A process according to claim 1, wherein the filter used in the filter sterilization is a membrane filter having a pore size of 0.22 pm.

20. A process according to claim 2, wherein the filter used in the filter sterilization is a membrane filter having a pore size of 0.22 pm.

21. A process according to claim 1, wherein the lactase solution is obtained by a method comprising:
  providing an untreated solution of lactase,
  separating poly and oligosaccharides from the untreated lactase solution to obtain a treated lactase solution, and
  adding 10 to 70 w/w % of glycerol to the treated lactase solution,
  wherein the poly and oligosaccharides are separated from the untreated lactase solution by applying one chromatographic step and wherein an anion exchange resin or a cation exchange resin or a hydrophobic interaction medium is used.

22. A process according to claim 2, wherein the lactase solution is obtained by a method comprising:
  providing an untreated solution of lactase,
  separating poly and oligosaccharides from the untreated lactase solution to obtain a treated lactase solution, and
  adding 10 to 70 w/w % of glycerol to the treated lactase solution,
  wherein the poly and oligosaccharides are separated from the untreated lactase solution by applying one chromatographic step and wherein an anion exchange resin or a cation exchange resin or a hydrophobic interaction medium is used.

\* \* \* \* \*